(12) United States Patent
Katkov et al.

(10) Patent No.: US 9,554,572 B2
(45) Date of Patent: Jan. 31, 2017

(54) PORTABLE DEVICE AND METHOD FOR CRYOPRESERVATION OF CELLS ENCAPSULATED IN IMMUNOISOLATING DEVICES

(71) Applicant: Celltronix, San Diego, CA (US)

(72) Inventors: Igor Katkov, San Diego, CA (US); Vladimir Fedorovich Bolyukh, Kharkov (UA); Pamela Itkin-Ansari, Carlsbad, CA (US)

(73) Assignee: Celltronix, San Diego, CA (US)

( * ) Notice: Subject to any disclaimer, the term of this patent is extended or adjusted under 35 U.S.C. 154(b) by 107 days.

(21) Appl. No.: 14/557,420

(22) Filed: Dec. 1, 2014

(65) Prior Publication Data

US 2015/0150241 A1   Jun. 4, 2015

Related U.S. Application Data

(60) Provisional application No. 61/910,263, filed on Nov. 29, 2013.

(51) Int. Cl.
*A01N 1/00* (2006.01)
*C12M 3/00* (2006.01)
*A01N 1/02* (2006.01)

(52) U.S. Cl.
CPC .................................. *A01N 1/0257* (2013.01)

(58) Field of Classification Search
CPC ...... C12M 21/08; A01N 1/021; A01N 1/0242; A01N 1/0273; A01N 1/0268
See application file for complete search history.

(56) References Cited

U.S. PATENT DOCUMENTS

| | | | |
|---|---|---|---|
| 7,162,888 B2 * | 1/2007 | Shu | B25J 11/00 378/208 |
| 7,197,884 B2 * | 4/2007 | Jones | A01N 1/02 62/86 |
| 7,527,764 B2 * | 5/2009 | Angelantoni | F25D 25/00 221/210 |
| 7,540,168 B2 * | 6/2009 | Schumann | A01N 1/02 62/378 |
| 9,097,691 B2 * | 8/2015 | Onizawa | G01N 35/026 |
| 2012/0255313 A1 * | 10/2012 | Katkov | F25D 3/102 62/51.1 |
| 2014/0069119 A1 * | 3/2014 | Katkov | F25D 3/10 62/51.1 |

* cited by examiner

*Primary Examiner* — Nathan Bowers
(74) *Attorney, Agent, or Firm* — Thibault Patent Group

(57) ABSTRACT

Embodiments of a cryopreservation device and method of use are described that allow cryopreserved samples to be transferred from one location to another. In one embodiment, a cryopreservation device comprises two, telescoping tubes; one for plunging biological material into a reservoir of cryogenic liquid refrigerant, and the other for capturing the biological material along with some of the liquid refrigerant, for transferring the biological material to another location.

14 Claims, 9 Drawing Sheets

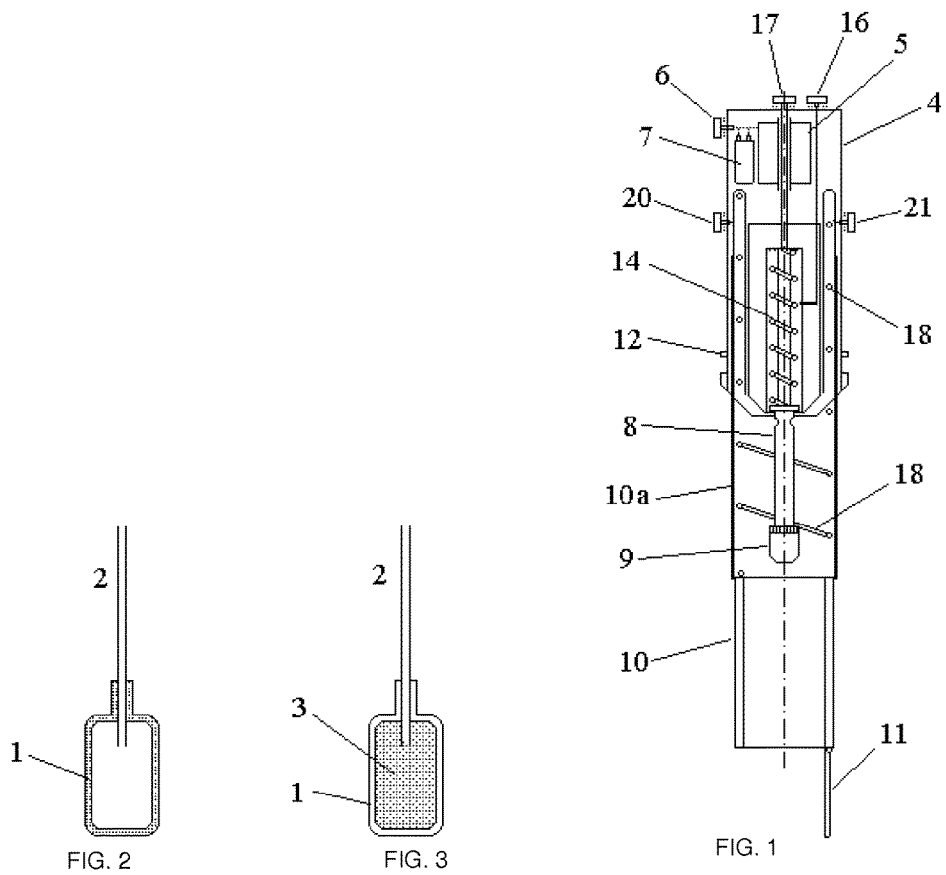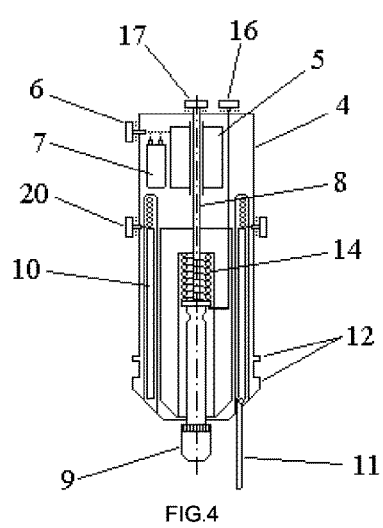

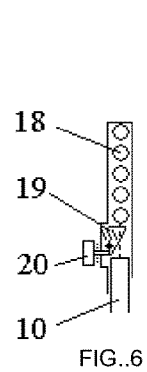
FIG. 6
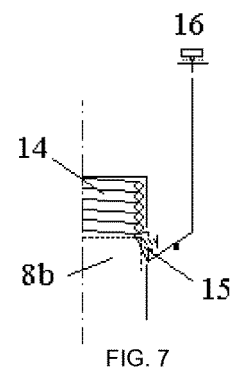
FIG. 7
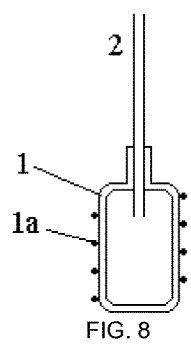
FIG. 8
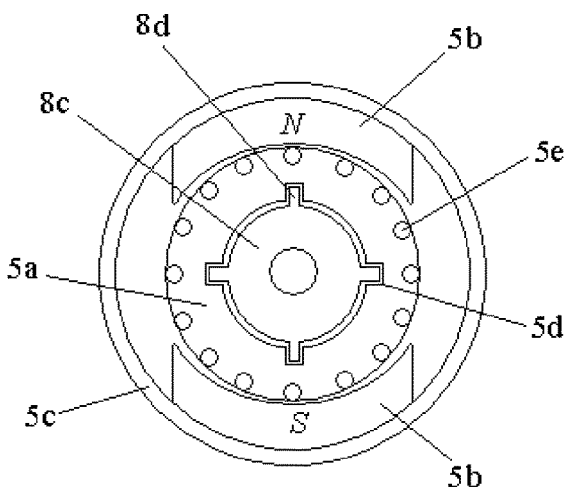
FIG. 9      FIG. 10
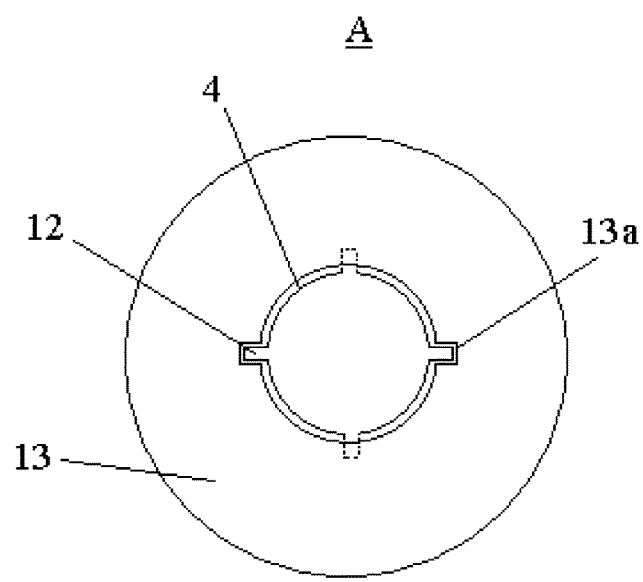

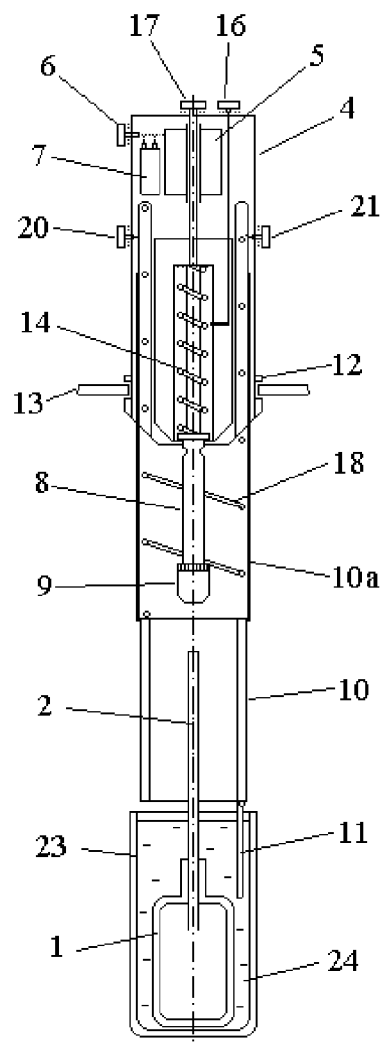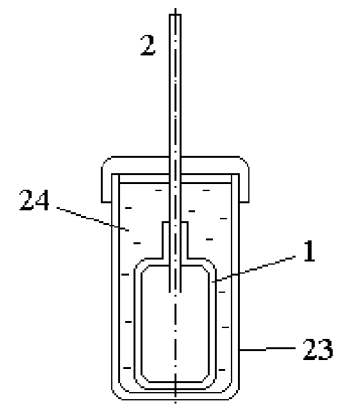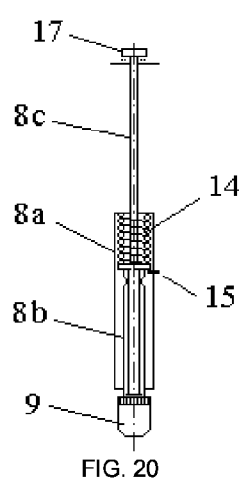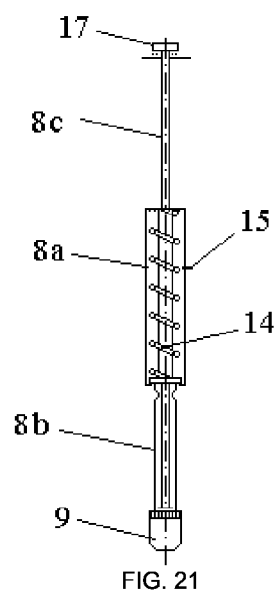
FIG. 18
FIG. 19
FIG. 20
FIG. 21

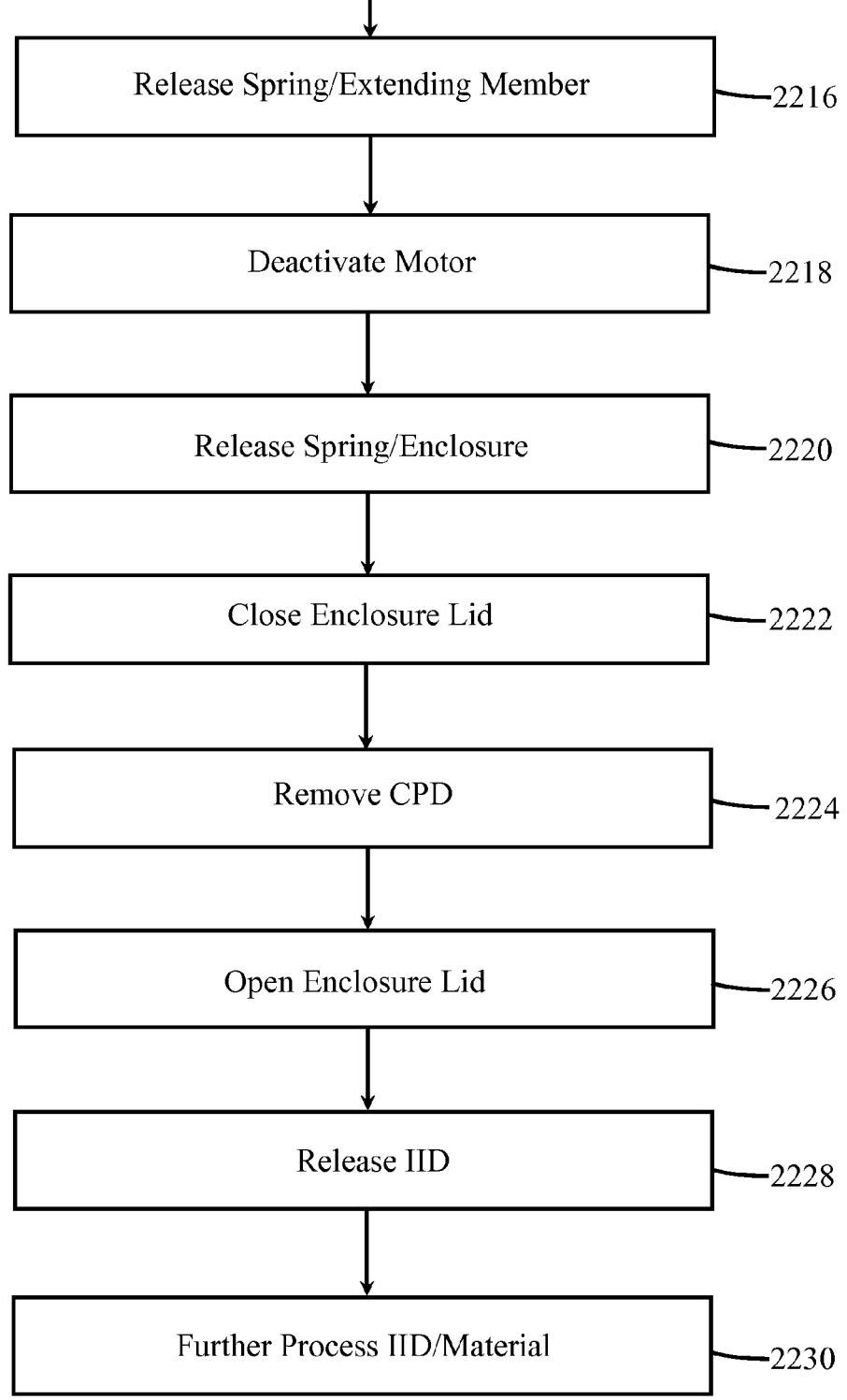

PORTABLE DEVICE AND METHOD FOR CRYOPRESERVATION OF CELLS ENCAPSULATED IN IMMUNOISOLATING DEVICES

CROSS-REFERENCE TO RELATED APPLICATION

This application claims the benefit of U.S. Provisional Application No. 61/910,263, filed on Nov. 29, 2013.

BACKGROUND

Field of Use

The present application relates generally to cryopreservation and generally to fast cooling of biological material for use in industries such as medicine, animal husbandry, and biomedical science.

Description of the Related Art

Cryopreservation is a process where biological materials, such as cells, tissues, or entire organs are preserved by cooling them to sub-zero temperatures. At low enough temperatures, any enzymatic or chemical activity which might cause damage to the biological material is effectively halted. Cryopreservation methods seek to reach low temperatures without causing additional damage caused by the formation of ice during freezing. Traditional cryopreservation has relied on coating the material to be frozen with a class of molecules termed cryoprotectants.

Cryofixation is a similar technique for fixation or stabilization of biological materials at ultra-freezing temperatures. This method involves ultra-rapid cooling of small biological samples to the temperature of liquid nitrogen (−196° C.) or below, stopping all motion and metabolic activity, and preserving the internal structure of cells by freezing all fluid phases solid. The ultimate objective is to freeze the specimen so rapidly (at 104 to 106 K per second) that ice crystals are unable to form, or are prevented from growing big enough to cause damage to the specimen's ultrastructure. The formation of samples containing specimens in amorphous ice is considered by some to be the holy grail of biological cryomicroscopy.

One method used to accomplish cryofixation is literally "plunging" biological material into to vial of very cold liquid refrigerant. In this technique, a small vial of ethane may be placed inside a larger liquid nitrogen reservoir. Then, a plunger is positioned over the reservoir, the plunger having an electron microscopy (EM) grid positioned at the bottom of the plunger. The EM grid comprises biological material to be frozen. The plunger has a heavy weight at the top that drives the plunger in a downward direction, forcing the EM grid into the ethane very quickly. When the EM grid enters the liquid ethane, the biological sample is frozen very rapidly, and then the grid can be moved to a storage box in liquid nitrogen for later use, for example, examination under an electron-microscope.

There are a number of drawbacks, however, to the technique described above. First and foremost, the plunger and reservoir must be precisely aligned with one another, and the length of travel by the plunger must be precisely controlled. This often results in a bulky, fixed device (e.g., non-portable) that is not capable of transferring the biological material to another location. Transferability may be desired, for example, the ability to transfer the biological material to another location along with some of the liquid refrigerant to keep the biological material as cold as possible during the transfer.

SUMMARY

The embodiments described herein relate to a cryopreservation apparatus and methods of operating the cryopreservation apparatus. In one embodiment, a cryopreservation apparatus is described, comprising a cylindrical body, a telescopic rod disposed within the cylindrical body, the telescopic rod comprising an elongated hollow structure, a first spring located within the elongated hollow structure and in communication with an extending member for at least partially ejecting the extending member from the elongated hollow structure, and a grasping mechanism for securing an immunoisolating device containing the material to the extending member, a enclosure, and a second spring in communication with the enclosure for at least partially ejecting the enclosure from the body, wherein the immunoisolating device is plunged into in a reservoir of cryogenic liquid refrigerant when the first spring is released, and the enclosure encapsulates the immunoisolating device after the immunoisolating device has been plunged into the reservoir.

BRIEF DESCRIPTION OF THE DRAWINGS

The features, advantages, and objects of the present invention will become more apparent from the detailed description as set forth below, when taken in conjunction with the drawings in which like referenced characters identify correspondingly throughout, and wherein:

FIG. 1 is a side, cut-away view of one embodiment of a cryopreservation device (CPD) used for preservation of biological materials;

FIG. 2 is a side view of an immunoisolating device (IID) and an insertion tube for storage of biological material, used in conjunction with the cryopreservation device of FIG. 1;

FIG. 3 is a side view of the immunoisolating device and insertion tube of FIG. 2, shown filled with biological material;

FIG. 4 is a side, cut-away view of the cryopreservation device shown in FIG. 1, configured for use;

FIG. 5 is a side, cut-away view of the cryopreservation device shown in FIG. 1 configured for use, including the immunoisolating device, insertion tube and biological material shown in FIGS. 2 and 3, and further including a protective device;

FIG. 6 is a close-up, side, cut-away view of one side of a body of the cryopreservation device shown in FIG. 1, showing a cross-section of coils of a spring located therein and compressed by a enclosure, and an interference mechanism operated by an activation mechanism;

FIG. 7 is a close-up, side, cut-away view of a spring compressed by a telescopic rod as part of the cryopreservation device of FIG. 1;

FIG. 8 is a side view of the immunoisolating device and insertion tube of FIG. 2, shown with spirally-wrapped lugs/external gripping belt;

FIG. 9 is a top, cut-away view of an electric motor as part of the cryopreservation device of FIG. 1, and the telescopic rod shown in FIG. 7;

FIG. 10 is a top, plan view of the protective device shown in FIG. 5;

FIG. 18 is a side, cut-away view of the cryopreservation device of FIG. 1, after being positioned above the second location, as shown in FIG. 17, and after the immunoisolating device and the biological material have been placed into the second reservoir;

FIG. 19 is a side, cut-away view of the immunoisolating device, tube, and biological material resting inside the second reservoir after having been released by the cryopreservation device of FIG. 1;

FIG. 20 is a side, cut-away view of the telescopic rod shown in FIG. 7, shown in an initial, compressed state;

FIG. 21 is a side, cut-away view of the telescopic rod shown in FIG. 7, shown in a second, extended state.

DETAILED DESCRIPTION

Figure 11:
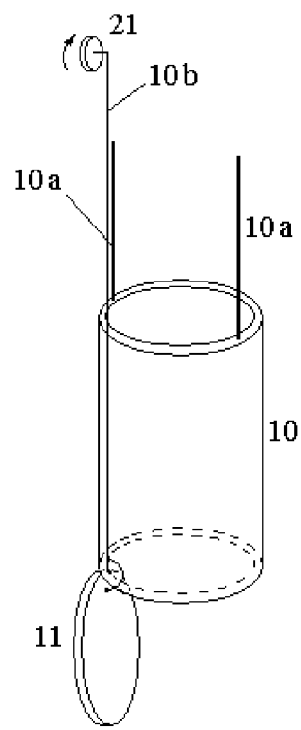
FIG. 11 is a perspective view of the enclosure shown in FIG. 6 having an open lid and guiding mechanisms.

The present application discusses various embodiments of an invention related to a method and apparatus for fast cryogenic cooling and transport of biological materials. Such embodiments may be used in industries such as medicine, animal husbandry, and biomedical science. Other industries where fast cooling may be of benefit is the semi-conductor industry, and metallurgy, for achieving a glassy state of metals and metal alloys. Such cooling may find application in other industries as well. Although this application discusses methods and apparatus of achieving fast cooling and transport in terms of biological materials, it should understood that such description is merely one example of how the principles and ideas described herein may be used.

In general, various embodiments of a cryogenic cooling and transport device are described, which allows for easy and effective cryopreservation of biological materials, while also allowing transferability of the biological material to other locations. In one embodiment, this is achieved by using a portable, hand-held cryopreservation device comprising two telescoping tubes or hollow structural channels; one for plunging the biological material into a reservoir of cryogenic liquid refrigerant, and the other for capturing the biological material along with an amount of the cryogenic liquid refrigerant in order to maintain the cryogenic temperature of the material as it is transferred to another location.

FIG. 1 illustrates a side, cut-away view of one embodiment of a cryopreservation device (CPD) 100 used for preservation and transport of biological materials. In this embodiment, CPD 100 is a portable device, allowing biological material to be frozen in one location and transferred to a second location along with some of the cryogenic liquid refrigerant used to freeze the biological material. In another embodiment, CPD 100 is fixed and non-portable. In one embodiment, CPD 100 is approximately 50 cm in length, having a diameter of approximately 8 cm. In other embodiments or applications, the dimensions of CPD 100 could be larger or smaller.

CPD 100 comprises telescopic rod 8, shown separately in FIGS. 20 and 21 and as part of CPD 100 in at least FIG. 1. Telescopic rod 8 comprises two co-axial structures or members 8a and 8b, spring 14, interference mechanism 15, rod 8c coupled to elongated hollow structure 8a, and grasping mechanism 9. Spring 14 is located inside elongated hollow structure 8a and is in communication with extending member 8b as extending member is pushed up inside elongated hollow structure 8a and against spring 14 during an initialization process. A lower portion of spring 14 may be connected to an upper portion of extending member 8b.

FIG. 20 shows telescopic rod 8 in a compressed position, while FIG. 21 shows telescopic rod 8 in an extended position. Spring 14 is held compressed by interference mechanism 15, which may comprise a tab, knob, elastic ratchet clamp or other structure that interferes with spring 14's ability to decompress or un-spring as spring 14 is compressed when extending member 8b is manually pushed inside of elongated hollow structure 8a during initialization. Interference mechanism 15 is coupled to, and operated by, activation mechanism 16, best shown in FIG. 7, which is a close-up, side, cut-away view of spring 14 compressed by extending member 8b. Extending member 8b moves from the position shown in FIG. 21 to the position shown in FIG. 20 by operating activation mechanism 16, causing interference mechanism 15 to release spring 14. Thus, extending member 8b is at least partially, forcefully ejected from elongated hollow structure 8a upon operation of activation mechanism 16. The speed at which extending member 8b is ejected from elongated hollow structure 8a is at least partially dependent on a spring constant of spring 14. A high spring constant causes extending member 8b to be ejected more quickly by spring 14 than a lower spring constant. By selecting spring 14 with particular spring constant, the speed at which extending member 8b is ejected can be selected. This speed may be a critical factor in successful cryogenic biological freezing.

Grasping mechanism 9 generally comprises a spring-loaded mechanism that is normally forced into a closed position by an internal spring (not shown). It may comprise two, three, or more grasping structures that form a "pincer". Grasping mechanism 9 is forced open by operation of mechanism 17 (such as a pushbutton), which, in one embodiment, is mechanically coupled to grasping mechanism 9 through rod 8c, spring 14/elongated hollow structure 8a, and extending member 8b. Extending member 8b is hollow, or alternatively comprises a channel, through which the mechanical coupling passes. Thus, by operation of mechanism 17, grasping mechanism 9 opens and closes, allowing grasping mechanism 9 to grasp objects, as will be described shortly.

In one embodiment, rod 8c extends from elongated hollow structure 8a to a rotor 5a of electric motor 5 for rotation by electric motor 5 during use of CPD 100. In this embodiment, rod 8c may comprise one or more "tabs" or "lugs" 8d formed on the surface of rod 8c for engagement with rotor 5a, as shown in FIG. 9, allowing electric motor 5 to turn telescopic rod 8. In other embodiments, rod 8c does not couple directly to rotor 5a, but is rather coupled to rotor 5a via a coupling mechanism, such as a gear, pulley, chain, band, etc.

CPD 100 further comprises enclosure 10, in this example comprising a cylindrical structure with a lid, or end, 11. Enclosure 10 is designed to surround and encapsulate a sample of biological material, including some cryogenic liquid refrigerant, when frozen biological material is transferred from one location to another. Although enclosure 10 is shown in the drawings as cylindrical in shape having a circular-cross section, it could comprise other shapes in the alternative having, for example, a square or rectangular cross-section. The enclosure 10 is typically made from one or more well-known insulating materials for keeping liquid refrigerant as cold as possible during transfer of the biological material, such as glass, fiber, plastic, etc. During initial operation, enclosure 10 is pushed up into body 4 of CPD 100, where it is in communication with spring 18 thereby compressing spring 18, as shown in FIGS. 4, 5, 6, and 13. FIGS. 1, 14, 15, 16, and 17 show spring 18 in an uncompressed state when enclosure 10 has been at least partially ejected from body 4 by spring 18.

Similar to spring 14 described above, spring 18 is compressed as enclosure 10 is pushed up into body 4, best shown in FIG. 6. FIG. 6 illustrates a close-up, side, cut-away view of one side of body 4, showing a cross-section of the coils of spring 18 compressed by enclosure 10, and interference mechanism 19 operated by activation mechanism 20 (e.g., a mechanical push-button). As spring 18 is compressed by enclosure 10, the coils of spring 18 pass interference mechanism 19, which retains spring 18 and prevents it from uncoiling or unspringing as it is compressed by enclosure 10. Interference mechanism 19 comprises a tab, knob, elastic ratchet clamp, or other mechanism that extends inside body 4 to retain spring 18. Activation mechanism 20 is mechanically coupled to interference mechanism 19 and causes interference mechanism 19 to release spring 18 when activation mechanism 20 is depressed or otherwise operated, causing enclosure 10 to be at least partially ejected from body 4 as spring 18 is released and uncoiled. The speed at which enclosure 10 is ejected from body 4 may be at least partially dependent on a spring constant of spring 18, as described above with respect to spring 14.

Guide mechanisms 10a may be used to guide enclosure 10 as it travels into and out of body 4 and/or to guide and/or support enclosure 10 after it has been ejected from body 4. These guide mechanisms 10a may take the form of wires or rails or any other mechanical guiding mechanism.

Figure 12:
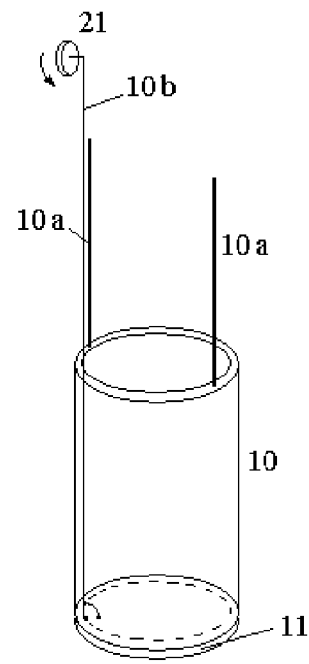
FIG. 12 is a perspective view of the enclosure, lid, and guiding mechanisms shown in FIG. 11, with the lid in an closed position.

Enclosure 10 comprises lid 11 that, in this example, is hingedly coupled to enclosure 10 via a small hinge. In another embodiment, lid 11 is coupled to enclosure 10 by rotation about a pin assembly attached to enclosure 10. Lid 11 is used to surround and form an enclosure around an immunoisolating device (IID) 1 housing biological material after enclosure 10 has been positioned over IID 1 as a result of being ejected from body 4 by spring 18, as will be described shortly. Lid 11 may be opened and closed by operating mechanism 21 (e.g., a handle, crank, dial, etc.) mechanically coupled to lid 11 by coupling 10b, best shown in FIGS. 11 and 12. When mechanism 21 is operated, coupling 10b causes lid 11 to close by pulling lid 11 towards enclosure 10 and allows lid 11 to open when mechanism 21 is operated to cause coupling 10b to push lid 11 into an open position. In another embodiment, a spring is used to force lid 11 into an open position when mechanism 21 is operated.

CPD 100 may further comprise protective device 13, shown in FIGS. 5, 10, and 14-17. In this embodiment, protective device 13 comprises a relatively thin, circular disc placed over body 4 and held in place, in this embodiment, by lugs 12 that interfere with slots 13a formed in protective device 13, as shown in FIG. 10. Protective device 13 is designed to shield operators from damaging liquid refrigerants that may splash while operating CPD 100. It may be comprise any rigid or semi-rigid material(s), such as thick foam plastic, plastic, hard rubber, wood, or any other material that can prevent liquid refrigerant from splashing an operator of CPD 100. In one embodiment, the diameter of protective device 13 is approximately 30 cm, in an embodiment where CPD 100 comprises a diameter of approximately 8 cm. Although shown in the figures as a circular structure, protective device 13 could comprise other geometric shapes.

It should be understood that although CPD 100 has been shown and described thus far a cylindrical or tubular object (e.g., a hollow tube having a circular cross-section), in other embodiments, it could comprise a structure and components that have different cross-sections, such as a square, rectangular, triangular, oval, or other, cross-section, sometimes referred to as "hollow structural channels". Thus the word "cylindrical" should not be limited to only a circular cross-section. In other embodiments, some of the components could have cross-sections of one geometry and other components having a different geometric cross-section. For example, body 4 and enclosure 10 could comprise a circular cross-section, as shown in the figures, while telescopic rod 8 could comprise structures 8a and 8b as square in cross-section.

CPD 100 may further comprise electric motor 5, shown in FIGS. 1, 4, 5, and 13-18. Electric motor 5 is used to rotate at least a portion of telescopic rod 8 after extending structure 8b has been at least partially ejected from body 4 during the cryogenic freezing process, as will be explained in greater detail below. Motor 5 is typically a direct current (DC) motor, operated by applying a voltage from battery 7 to the motor via switch 6. In one embodiment, motor 5 is configured to rotate at a fixed speed of between 1 and 120 RPM. In another embodiment, electric motor 5 is configurable to rotate between 1 and 120 RPM by varying the voltage applied to electric motor 5 using, for example, a variable-resistive switch and/or related circuitry well known in the art. Electric motor 5 is typically a relatively low-power device, as the torque needed to rotate telescopic rod 8 is typically low.

FIG. 9 is a top, plan, cut-away view of one embodiment of electric motor 5, comprising rotating rotor 5a and static stator 5b, containing north N and south S poles, secured on a body 5c. Rotor 5a may contain one or more axial slots 5d, for engagement with axial lugs 8d formed on rod 8c. Rotor 5a generally comprises windings 5e (shown in FIG. 9 in cross-section), which connects to constant voltage source 7 through switch 6. In one embodiment, telescopic rod 8, including rod 8c, is pushed in a downward direction, away from electric motor 5 upon actuation of mechanism 16, causing axial lugs 8d to pass through rotor 5a via axial slots 5d, while still allowing rotor 5a to act upon rod 8c, causing rotation of at least a portion of telescopic rod 8.

Figure 22:
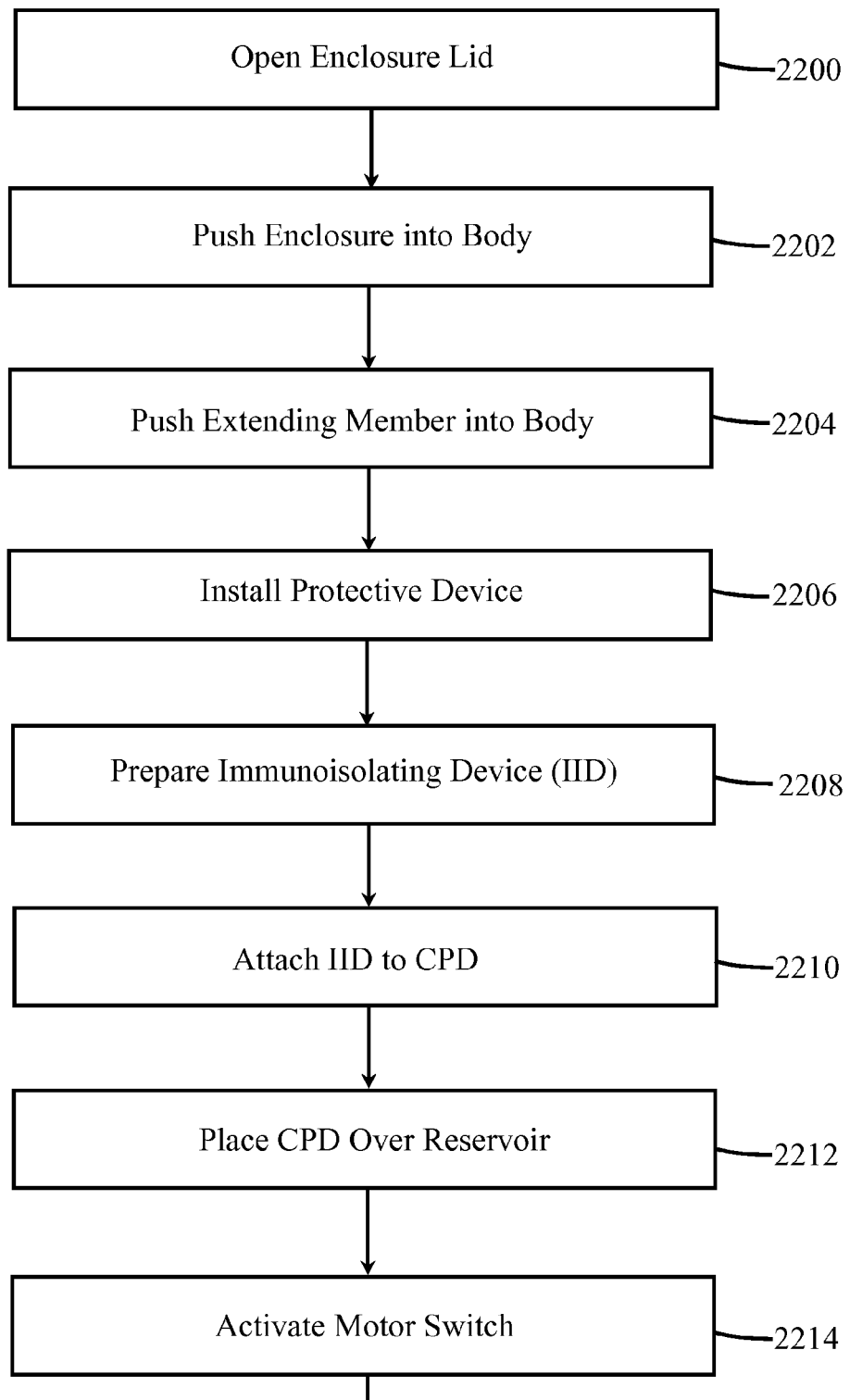
FIG. 22 is flow diagram illustrating one embodiment of a method for operating the cryopreservation device of FIG. 1.

FIG. 22 is flow diagram is flow diagram illustrating one embodiment of a method for operating CPD 100 shown in FIG. 1. It should be understood that in some embodiments, not all of the steps shown in FIG. 22 are performed and that the order in which the steps are performed may be different in other embodiments. It should be further understood that some minor method steps have been omitted for purposes of clarity.

At block 2200, mechanism 21 is operated, causing lid 11 to move to an open position, as shown in FIG. 1.

At block 2202, enclosure 10 is pushed into body 4, compressing spring 18, as shown in FIGS. 4, 5, and 6. Spring 18 and enclosure 10 are held in place by interference mechanism 19 acting as interference to the coils of spring 18 and/or enclosure 10.

At block 2204, extending member 8b of telescopic rod 8 is pushed into elongated hollow structure 8a, compressing spring 14, as shown in FIGS. 4, 5, 7, and 20. As the spring is being compressed, the coils of the spring pass interference mechanism 15 (upward) while being prevented from moving in the opposite direction (downward).

At block 2206, protective device 13 is placed over body 4 of CPD 100 and secured onto body 4 by fastening means such as the tab and slot arrangement described above with respect to FIG. 11, or in any other manner well-known in the art. At this point, CPD 100 is configured for use.

At block 2208, in an embodiment where biological material such as cells or tissue are being preserved, an immunoisolating device (IID) 1 is prepared. In other embodiments, a receptacle or "holding device" may be prepared for retaining an object to be frozen, such as a compound, a metal, a semi-conductor, etc. IIDs are well-known in the art for holding biological materials such as blood and blood components, tissue samples, etc. The bags may come in many different sizes and shapes and may comprise spirally-wrapped lugs or one or more external gripping belts 1a attached to, or formed on, an exterior of IID 1, as shown in FIG. 8. In one embodiment, the lugs 1a are created by wrapping IID 1 with tape strands. The lugs 1a on IID 1 help promote heat transfer from cryogenic liquid refrigerant 24 to biological material 3 inside the IID.

Continuing with bag preparation, IID 1 is placed into a vitrified solution at room temperature for a predetermined time, such as one hour, allowing IID 1 to become saturated with the vitrified solution. Next, an insertion tube 2 is inserted into the neck of IID 1, typically held in place by the physical dimensions of the neck and tube 2 and/or the neck made of a material having an elastic characteristic. Next, biological material 3 is inserted into IID 1 via tube 2. Then, IID 1 is transferred to a cold location, such as a freezer, to bring the IID and biological material 3 to a temperature of, for example, zero degrees C.

After a predetermined time period, such as after five to ten minutes, a cryoprotectant is added to the biological material 3, in one embodiment, by saturating the exterior of cryoprotection bag 1 with the cryoprotectant. Cryoprotectants are well-known in the art to protect biological tissue from damage due to freezing, e.g., protection against ice-crystal formation in cellular structures. Glycerol and ethylene glycol are well-known cryoprotectants. During this time, biological material 3 becomes saturated with the cryoprotectant.

At block 2210, IID 1, loaded with biological material 3 protected by the cryoprotectant, is attached to CPD 100 by operating mechanism 17, causing grasping mechanism 9 to open. Tube 2 is placed into grasping mechanism 9, and then mechanism 17 is released, causing grasping mechanism 9 to close, thereby securing tube 2 and IID 1, to the end of extending member 8b, as shown in FIG. 5. FIG. 5 is a side, plan, cut-away view of CPD 100 with IID 1 attached to it via tube 2. It also shows protective device 13 in place, and springs 14 and 18 compressed by extending member 8b and enclosure 10, respectively, locked into place by interference mechanism 15 and interference mechanism 19, respectively.

At block 2212, an operator of CPD 100, such as a laboratory technician, places the IID 1 over an opening of a liquid refrigerant reservoir 22, filled with a cryogenic liquid refrigerant 24 such as cryogenic liquid nitrogen, in an embodiment where CPD 100 is hand-held and portable. In an embodiment where CPD 100 is fixed, liquid refrigerant reservoir 22 may be positioned underneath CPD 100.

At block 2214, switch 6 is activated, causing electric motor 5 to begin rotating at least a portion of telescopic rod 8 as described previously, thus also rotating IID 1 with its biologic material.

Figure 13:
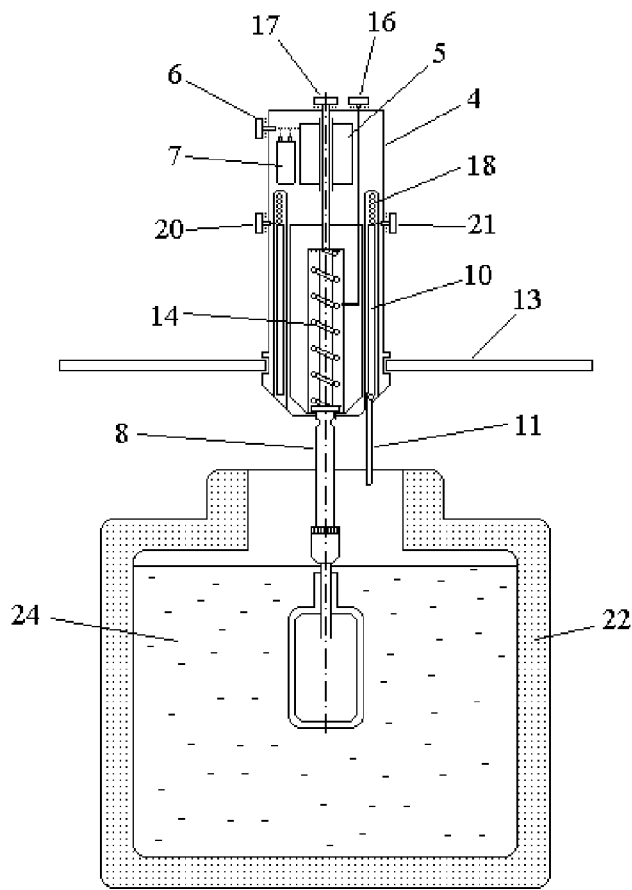
FIG. 13 is a side, cut-away view of the cryopreservation device of FIG. 1 after the spring shown in FIG. 7 has been released, immersing the immunoisolating device and biological material into a liquid refrigerant reservoir filled with a cryogenic liquid refrigerant.

At block 2216, activation mechanism 16 is operated, causing interference mechanism 15 to open, releasing spring 14 and causing spring 14 to uncoil. Spring 14 acts on extending member 8b, forcing extending member 8b, along with IID 1, downwards and at least partially ejecting extending member 8b from elongated hollow structure 8a, plunging IID 1 into liquid refrigerant reservoir 22 and the cryogenic liquid refrigerant 24, as shown in FIG. 13. Depending on the spring constant of spring 14, ejection of extending member 8b may occur rapidly, for example, 200 milliseconds. When this happens, in one embodiment, rod 8c is also forced downward, causing axial lugs 8d to pass through rotor 5a via axial slots 5d, while still allowing rotor 5a to act upon rod 8c, continuing rotation of at least a portion of telescopic rod 8.

Biological material 3 in IID 1 is rapidly cooled as a result of being immersed in cryogenic liquid refrigerant 24. Cooling is enhanced by rotation of IID 1 as extending member 8b and/or telescopic rod 8 is rotated by electric motor 5. The rotation helps reduce the Leidenfrost effect, which is a phenomenon in which a liquid, in near contact with a mass significantly hotter than the liquid's boiling point, produces an insulating vapor layer that keeps the liquid from boiling rapidly. Thus, the rotation increases the cooling speed of IID 1 and, therefore, successful freezing of biological material 3.

At block 2218, at some time after immersion of IID 1 in cryogenic liquid refrigerant 24, electric motor 5 may be deactivated by operation of switch 6, causing rotor 5a, elongated hollow structure 8a and/or 8b, IID 1 and biological material 3 to stop rotating. Electric motor 5 may be deactivated when biological material 3 has been cooled to a desired temperature based on parameters such as the amount of biological material 3 to be cooled, the temperature of the cryogenic liquid refrigerant 24, the time that IID 1 has been immersed in cryogenic liquid refrigerant 24, and the rotational speed of electric motor 5.

Figure 14:
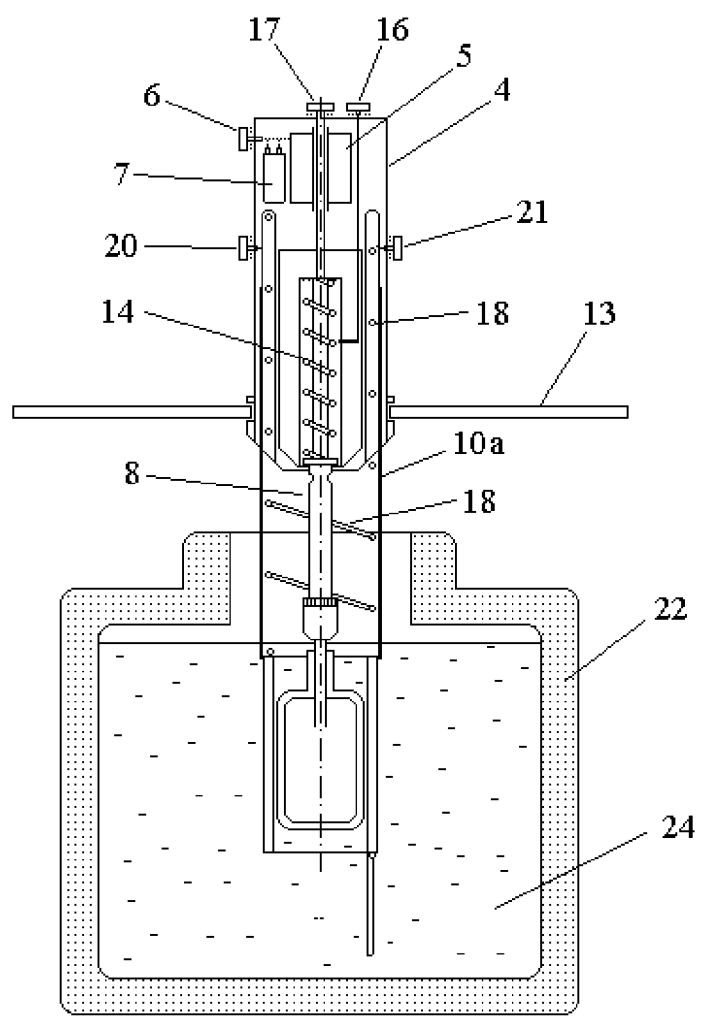
FIG. 14 is a side, cut-away view of the cryopreservation device of FIG. 1 after the spring shown in FIG. 7 has been released and further after the spring shown in FIG. 6 has been released, causing the enclosure shown in FIG. 6 to encapsulate the immunoisolating device and biological material.

At this point, after IID 1 and biological material 3 have been cooled to a desired temperature, it may be desirable to transfer IID 1 to another location, for example, from reservoir 22 to another location 23, such as a different room, from reservoir 22 to a test tube, from reservoir 22 to another reservoir, etc. It may be further desirable to maintain the cooled temperature of IID 1 during the transfer. Thus, at block 2220, activation mechanism 20 is operated, causing interference mechanism 19 to release spring 18, thereby at least partially ejecting enclosure 10 out from body 4, accelerating it downwards towards reservoir 22, and plunging it into the cryogenic liquid refrigerant 24, surrounding IID 1, as shown in FIG. 14. At this time, in one embodiment, enclosure 10 may be supported by guide members 10a.

Figure 15:
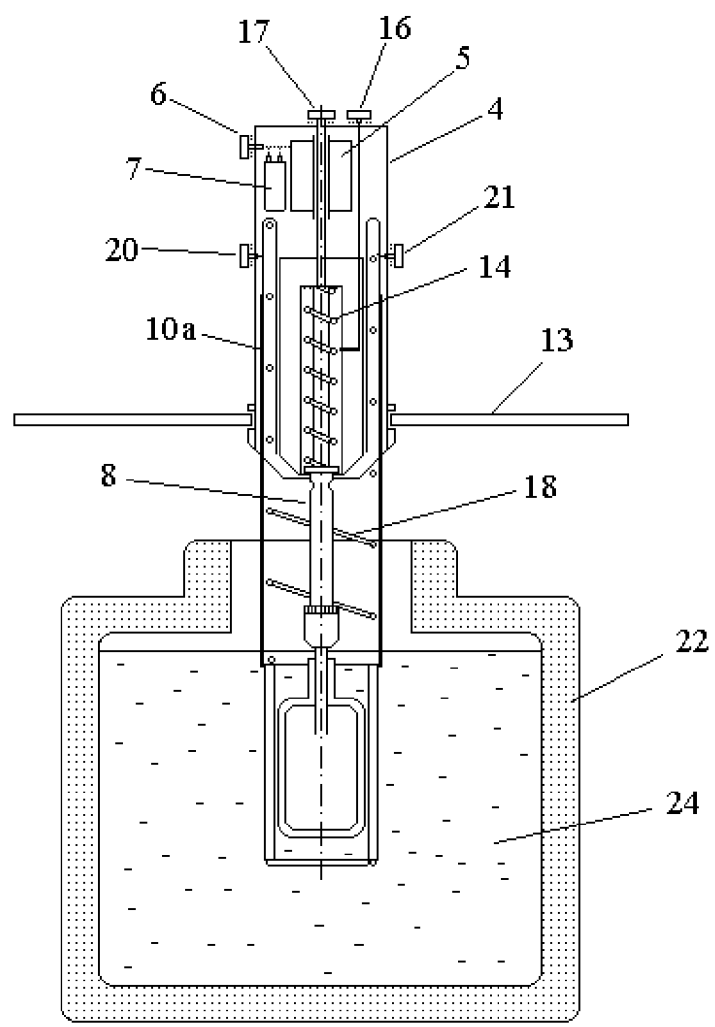
FIG. 15 is a side, cut-away view of the cryopreservation device of FIG. 1 after the spring shown in FIG. 7 has been released, and further after the spring shown in FIG. 6 has been released, and further after the lid shown in FIG. 11 of the enclosure shown in FIGS. 6 and 11 has been closed, encapsulating the immunoisolating device and biological material along with some of the cryogenic liquid refrigerant shown in FIGS. 13 and 14.
Figure 16:
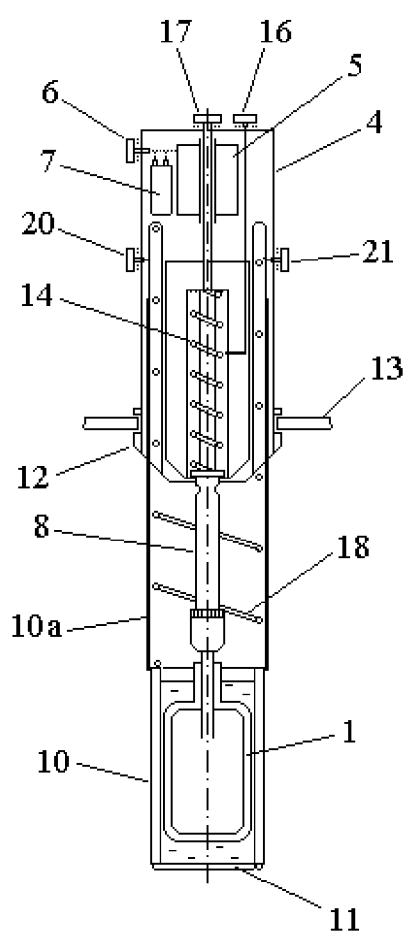
FIG. 16 is a side, cut-away view of the cryopreservation device of FIG. 1 after the immunoisolating device and biological material have been encapsulated by the enclosure shown in FIGS. 6 and 11 as the immunoisolating device and biological material is being transferred from the liquid refrigerant reservoir shown in FIGS. 13-15 to another location.

At block 2222, mechanism 21 is operated, causing traveling rod 10b to pull lid 11 closed against the bottom, open end of enclosure 10, as shown in FIG. 15. This, in effect, creates a portable vessel containing IID 1 and some of the cryogenic liquid refrigerant 24 captured as lid 11 was closed.

Figure 17:
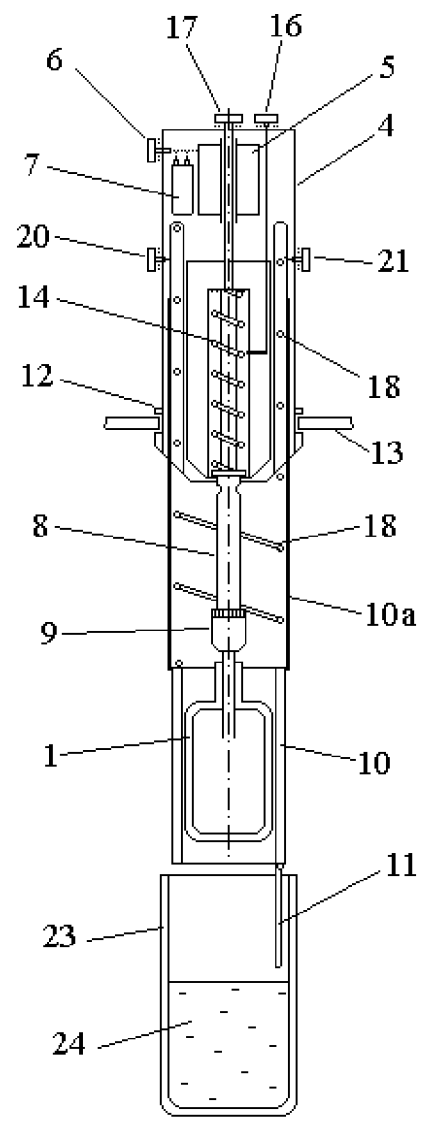
FIG. 17 is a side, cut-away view of the cryopreservation device of FIG. 1, after transferring the immunoisolating device and the biological material to another location, positioned above a second reservoir, with the lid shown in FIG. 11 in an open position.

At block 2224, CPD 100 is lifted away from reservoir 22, taking IID 1, surrounded by some of the cryogenic liquid refrigerant 24 captured by enclosure 10/lid 11, along with it. IID 1 may then be transferred to another location 23, such as a sterile room, under a laminar flow box, a second reservoir having the same or different cryogenic liquid refrigerant that was in reservoir 22, or a test tube or other receptacle, as shown in FIG. 17.

At block 2226, mechanism 21 is operated, causing lid 11 to open. This may occur as IID 1 is located above the second reservoir, test tube, or other receptacle, also shown in FIG. 17, or it may occur after immersion in the second cryogenic liquid refrigerant.

At block 2228, the IID is released from CPD 100 by operation of mechanism 17, causing grasping mechanism 9 to open and release tube 2, as shown in FIG. 18. IID 1 may then fall into the second reservoir and/or fall to the bottom of the second reservoir.

At block 2230, after IID 1/tube 2 has been removed from CPD 100, the biological material inside IID may be packaged for shipment, prepared for research, or otherwise readied for further processing, as shown in FIG. 19.

While the foregoing disclosure shows illustrative embodiments of the invention, it should be noted that various changes and modifications could be made herein without departing from the scope of the invention as defined by the appended claims. The functions, steps and/or actions of the method claims in accordance with the embodiments of the invention described herein need not be performed in any particular order. Furthermore, although elements of the invention may be described or claimed in the singular, the plural is contemplated unless limitation to the singular is explicitly stated.

We claim:

1. A cryopreservation apparatus for cryogenically preserving material, comprising:
    a body;
    an extending member disposed at least partially inside the body in a first position and at least partially outside the body in a second position;
    means coupled to the extending member for securing an immunoisolating device containing the material to the extending member;
    an elongated enclosure disposed at least partially inside the body in a first position and at least partially outside the body in a second position;
    a spring disposed inside the body, comprising a first end in communication with a first end of the extending member for causing the extending member to move from the first position to the second position; and
    means for covering a first end of the elongated enclosure when the elongated enclosure is in the second position.

2. The cryopreservation apparatus of claim 1, further comprising:
    an elongated hollow structure disposed inside the body for receiving the extending member;
    wherein the spring is disposed inside the elongated hollow structure.

3. The cryopreservation apparatus of claim 1, further comprising:
    an interference mechanism for holding the extending member in the first position, and for releasing the extending member when a user of the cryopreservation device operates a mechanism in communication with the interference mechanism, causing the extending member to be pushed into the second position by the spring.

4. The cryopreservation apparatus of claim 1, wherein the means for securing an immunoisolating device to the extending member comprises a grasping mechanism, and the cryopreservation apparatus further comprises:
    a mechanism for a user to open and close the grasping means;
    a channel formed longitudinally through the extending member; and
    a mechanical coupling connecting the mechanism to the grasping mechanism, for communicating mechanical actions of the mechanism to the grasping mechanism.

5. The cryopreservation apparatus of claim 1, further comprising:
    an electric motor for causing rotation of the extending member when the extending member is in the second position.

6. The cryopreservation apparatus of claim 1, further comprising:
    a shield mounted to an exterior of the body for protecting a user of the apparatus from being splashed by liquid refrigerant when the extending member travels from the first position to the second position.

7. A method of cryogenically preserving material, comprising:
    securing an immunoisolating device containing the material to an extending member;
    pushing the extending member into a body of a cryopreservation device against a spring, compressing the spring;
    pushing an elongated enclosure into the body;
    placing the cropreservation device over a reservoir of liquid refrigerant;
    releasing the spring, causing the extending member to extend from the body, causing the immunoisolating device to be plunged into the reservoir;
    releasing the elongated enclosure, causing the elongated enclosure to be plunged into the reservoir, surrounding the immunoisolating device; and
    covering one end of the elongated enclosure to form a portable vessel containing some of the liquid refrigerant and the immunoisolating device.

8. The method of claim 7, further comprising:
    operating an electric motor within the cryopreservation device that causes rotation of the extending member.

9. The method of claim 7, further comprising:
    installing a shield to the cryopreservation device to protecting a user of the cryopreservation device from being splashed by the liquid refrigerant when the extending member is released into the reservoir.

10. The method of claim 7, wherein pushing the extending member into the body of the cryopreservation device comprises pushing the extending member against a spring located within an elongated hollow structure within the cryopreservation device.

11. The method of claim 7, wherein pushing the elongated enclosure into the body comprises pushing the elongated enclosure against a spring located within the cryopreservation device.

12. The method of claim 7, wherein releasing the extending member comprises operating a mechanism that causes an interference mechanism to release the extending member, allowing a spring to uncoil against the extending member.

13. The method of claim 7, wherein releasing the elongated enclosure comprises operating a mechanism that causes an interference mechanism to release the elongated enclosure, allowing a spring inside the cryopreservation device to uncoil against the elongated enclosure.

14. The method of claim 7, wherein covering one end of the elongated enclosure comprises operating a mechanism that causes a coupling to a lid to close the lid against the one end of the elongated enclosure.

* * * * *